United States Patent [19]

Lim

[11] 3,935,342
[45] Jan. 27, 1976

[54] HYDROPHILIZATION OF NON-POLAR SURFACES

[75] Inventor: Drahoslav Lim, Palo Alto, Calif.

[73] Assignee: Merck Patent Gesellschaft mit beschrankter Haftung, Darmstadt, Germany

[22] Filed: Dec. 4, 1973

[21] Appl. No.: 421,718

Related U.S. Application Data

[63] Continuation-in-part of Ser. No. 331,093, Feb. 9, 1973.

[52] U.S. Cl. ............... 427/341; 427/387; 260/827
[51] Int. Cl.² ..................... C08F 8/10; C08J 5/24
[58] Field of Search... 117/138.8 E, 138.8 D, 138.8 A, 117/161 ZA, 118, 62.1; 427/341, 387; 260/827

[56] References Cited
UNITED STATES PATENTS

| | | | |
|---|---|---|---|
| 2,865,899 | 12/1958 | Hurwitz et al. | 260/79.7 |
| 2,956,044 | 10/1960 | Merker | 260/46.5 |
| 3,708,225 | 1/1973 | Misch et al. | 351/160 |

Primary Examiner—Cameron K. Weiffenbach
Assistant Examiner—Ralph E. Varndel
Attorney, Agent, or Firm—Millen, Raptes & White

[57] ABSTRACT

A hydrophobic polymer is hydrophilized by polymerizing thereon a compound having the formula

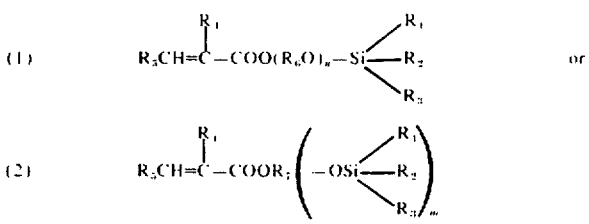

where $R_5$ is hydrogen or lower alkyl, $R_4$ is hydrogen, lower alkyl, halogen of atomic weight 9 to 80, phenyl or cyano, $R_6$ is alkylene or haloalkylene of 2 to 4 carbon atoms, $R_7$ is alkylene of 3 to 6 carbon atoms, $n$ is an integer of 1 to 4, $m$ is an integer of 2 to 5 and $R_1$, $R_2$ and $R_3$ are lower alkyl, phenyl or tolyl and thereafter hydrolyzing off the silyl groups. Silylated copolymers can also be prepared to form the hydrophilic coating.

22 Claims, No Drawings

HYDROPHILIZATION OF NON-POLAR SURFACES

This application is a continuation-in-part of application Ser. No. 331,093, filed Feb. 9, 1973.

Hydrophilization of only slightly polar (hydrophobic) polymers can be achieved by several methods, e.g., by coating with a layer of a hydrophilic polymer and if possible fixing it to the surface; by polymerizing a hydrophilic monomer on a hydrophobic polymer surface to be coated, or by grafting.

Formation of a layer of a hydrophobic material, e.g., a hydrophobic polymer, homogeneously with a hydrophilic polymer represents a very difficult procedure owing to slight mutual solubility due to the great difference in polarity and consequently in thermodynamic behavior, the hydrophilic monomers simply do not penetrate hydrophobic polymer substrates and it is difficult to coat the hydrophobic polymer.

It has now been found that this problem has been solved by treating a hydrophobic polymer substrate with a certain silylated acrylate or methacrylate monomer above or admixed with other copolymerizable ethylenically unsaturated monomers, polymerizing the monomer (or monomers) and then hydrolyzing under mild conditions to break the siloxy bonds and form free hydroxyl groups. The final product represents a material with a homogeneous layer of a hydrophilic material strongly adhered to a hydrophobic material.

The silylated monomer is hydrophobic and swells the hydrophobic polymeric substrate and penetrates it. When the monomer is polymerized an excellent bond and a thoroughly anchored intimate mixture is obtained. The silylated monomer is thin and spreads easily on the surface of the hydrophobic polymer.

The hydrolysis can be carried out in acid, e.g., sulfuric acid or acetic acid, alkali, e.g., sodium hydroxide, potassium hydroxide, sodium carbonate, water or water-solvent mixture.

By the process there can be made a thin uniform layer of strongly bonded hydrophilic coating on the hydrophobic polymer. There can also be prepared thick coatings or multiple coatings. The coating can be from submicron in thickness to 1 mil or even thicker, e.g., 5 mils.

The coated articles can be used wherever a hydrophilic coating is desired, e.g., in preparing contact lenses, prosthetic devices, catheters, venus tubes, common ducts, diaphragms, intrauterine devices, as non-fog coatings, blood containers and blood vessel substitutes, blood transmission tubes, non-static coatings on fibers, e.g., textiles or carpets or on phonograph records, bandages, packaged food containers, bristles, flavored drinking straws.

The hydrophobic materials which can be treated according to the invention are those in which the silylated monomers are capable of swelling or dissolving. The hydrophobic polymer need only take up 1% (or even less) of the silylated monomer. It can take up 3% or more of monomer. Actually, there is no maximum on the amount of monomer which can be absorbed or taken up by the polymer.

In some cases, e.g., with rubber, there appears to be a grafting of the silylated material to the hydrophobic polymer during the polymerization.

Examples of suitable hydrophobic polymers are natural rubber, silicone rubber (polydimethylsiloxane rubber, for example), polyisobutylene, butyl rubber (isoolefin-diolefin copolymers, e.g., isobutylene-butadiene copolymer and the other copolymers set forth in Thomas U.S. Pat. No. 2,356,128), polyethylene, polypropylene, ethylene propylene copolymers (e.g., 50:50, 80:20 and 20:80), ethylene-monoolefin copolymers wherein the monoolefin has four to 10 carbon atoms and is present in a minor amount, e.g., ethylene-butene-1 copolymer (95:5) and ethylene-decene-1 copolymer (90:10), styrene-butadiene rubber (SBR rubber), e.g., (75% butadiene, 25% styrene) and EPDM rubbers and acrylonitrile butadiene styrene terpolymers (ABS).

As the EPDM rubber there can be employed many of the commercially available EPDM rubbers. The EPDM rubber normally contains 30 to 70 molar percent (preferably 50 to 60 molar percent) of ethylene, 65 to 20 molar percent (preferably 35 to 45 molar percent propylene) and 1 to 15 molar percent (preferably 3 to 5 molar percent) of the nonconjugated polyolefin. Usually the polyolefin is not over 10 molar percent. The ethylene and propylene can each be 5 to 95 molar percent of the composition. The nonconjugated polyolefin includes aliphatic nonconjugated polyene hydrocarbons and cycloaliphatic nonconjugated polyene hydrocarbons, e.g., endocyclic dienes. Specific examples of suitable nonconjugated polyolefins include pentadiene-1,4, hexadiene-1,4, dicyclopentadiene, methyl cyclopentadiene dimer, cyclododecatriene, cyclooctadiene-1,5,5-methylene-2-norbornene.

Specifc examples of suitable terpolymers are the Royalenes which contain 55 mole percent ethylene, 40 to 42 mole percent propylene and 3 to 5 mole percent dicyclopentadiene; Enjay terpolymers, e.g., ERP-404 of Enjay and Enjay 3509 which contains about 55 mole percent ethylene, 41 mole percent propylene and 4 mole percent 5-methylene-2-norbornene; Nordel, a terpolymer of 55 mole percent ethylene, 40 mole percent propylene and 5 mole percent hexadiene-1,4. Another suitable terpolymer is the one containing 50 mole percent ethylene, 47 mole percent propylene and 3 mole percent 1,5-cyclooctadiene (Dutrel), rubbery butadiene-acrylonitrile copolymer, cis-isoprene polymer, polystyrene, styrene-acrylonitrile copolymer, polyalkyl acrylates and methacrylates, e.g., poly methyl methacrylate, polybutyl methacrylate, poly 2-ethylhexyl acrylate, polyvinyl chloride, and vinyl chloride copolymers, e.g., vinyl chloridevinyl acetate copolymer, polyvinylidene chloride, vinyl chloridevinylidene chloride copolymer, (e.g., 85:15), vinyl chlorideacrylonitrile copolymer (e.g., 85:15) polytetrafluoroethylene (Teflon), tetrafluoroethylene-hexafluoro-propylene copolymer, polytrifluoro-chloroethylene, polyvinylidene fluoride, nylon (e.g., nylon 6, nylon 6,6), Orlon (polyacrylonitrile), polyesters (e.g., polyethylene terephthalate).

The present invention utilizes silylated monomers of the formulae

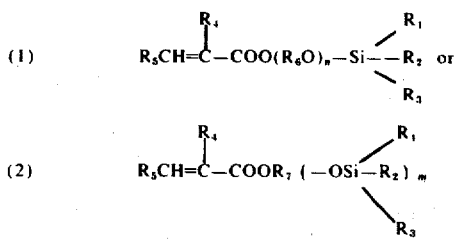

where $R_5$ is hydrogen or lower alkyl, e.g., 1 to 4 carbon atoms, $R_4$ is hydrogen, lower alkyl, e.g., methyl or ethyl, halogen of atomic weight 9 to 80, phenyl or cyano, $R_6$ is alkylene or haloalkylene of 2 to 4 carbon atoms, $R_7$ is alkylene of 3 to 6 carbon atoms, $n$ is an integer of 1 to 4, $m$ is an integer of 2 to 5 and $R_1$, $R_2$ and $R_3$ are alkyl of 1 to 6 carbon atoms, more preferably 1 to 4 carbon atoms, or phenyl or tolyl. Most preferably at least $R_1$ and $R_2$ are both alkyl.

Examples of such compounds are trimethylsiloxyethyl acrylate, trimethylsiloxyethyl methacrylate, trimethylsiloxypropyl acrylate, trimethylsiloxypropyl methacrylate, dimethylethylsiloxyethyl acrylate, dimethylphenylsioxyethyl acrylate, trimethylsiloxyethoxyethyl methacrylate, trimethylsiloxyethoxyethyl acrylate, trimethylsiloxyethoxyethoxyethyl methacrylate, trimethylsiloxypropoxypropoxypropyl acrylate, trimethylsiloxyethoxyethoxyethoxyethyl methacrylate, trimethylsiloxybutyl acrylate, trimethylsiloxybutyl methacrylate, triethylsiloxyethyl acrylate, tripropylsiloxyethyl methacrylate, tributylsiloxyethyl acrylate, penta (trimethylsiloxy) sorbityl methacrylate, tributylsiloxypropyl methacrylate, tris(trimethylsiloxy) neopentyl methacrylate, tris(dimethylethysiloxy) neopentyl acrylate, dimethylbutylsiloxyethoxyethyl methacrylate, bis(dimethylphenylsiloxy) neopentyl methacrylate, trihexylsiloxyethyl acrylate, bis (trimethylsiloxy) neopentyl acrylate, triphenylsiloxyethyl acrylate, triphenylsiloxyethyl methacrylate, tri-tolylsiloxyethyl methacrylate, bis(trimethylsiloxy) neohexyl acrylate, methylethylphenylsiloxyethyl acrylate, bis(trimethylsiloxy) neohexyl methacrylate, bis(trimethylsiloxy) propyl acrylate, bis(trimethylsiloxy) propyl methacrylate, bis(dimethylphenylsiloxy) propyl methacrylate, trimethylsiloxyethyl crotonate, triethylsiloxypropyl crotonate, trimethylsiloxyethoxyethyl crotonate, trimethylsiloxyethyl phenylacrylate, trimethylsiloxypropyl phenylacrylate, trimethylsiloxyethoxyethyl phenylacrylate, trimethylsiloxyethyl chloroacrylate, dimethylhexylsiloxyethyl chloroacrylate, diethylpropylsiloxyethoxyethyl chloroacrylate, trimethylsiloxyethyl fluoroacrylate, triethylsiloxyethoxyethyl fluoroacrylate, diethylphenylsiloxypropyl fluoroacrylate, trimethylsiloxyethyl bromoacrylate, trimethylsiloxyethyl cyanoacrylate, trimethylsiloxyethoxyethyl cyanoacrylate, trimethylsiloxypropoxypropyl methacrylate, diemthylphenylsiloxypropoxypropyl acrylate, trimethylsiloxy-2-chloropropyl methacrylate, trimethylsiloxy-2-bromopropyl acrylate.

Many hydroxyalkyl acrylates and methacrylates and related compounds as normally prepared contain the corresponding diacrylate and dimethacrylates as impurities. It is difficult to remove these materials and hence the polymers perpared almost invariably contain small amounts of such cross-linking agents, e.g., see Chromacek U.S. Pat. No. 3,597,473. By polymerizing the silylated materials according to the invention it is possible to provide hydrophobic polymers having a linear hydrophilic polymer coating by hydrolyzing the silylated polymer to form pure polymeric hydroxyalkyl acrylates or methacrylate polymer coating or the like devoid of the cross-linking diacrylates or methacrylates.

After polymerization, e.g., with free radical initiators or irradiation, it is possible by hydrolysis to recover easily polymer systems with a structure free of silylation.

The advantage of the temporary blocking of hydroxy groups results in a low polarity which, as stated is an important condition in order to have compatibility with the weakly polar hydrophobic polymer materials. By subsequent hydrolysis, as has been stated, it is possible to convert the silylated polymer in the next step into polymers with free hydroxy groups and which can have a linear structure if no cross-linking monomer is deliberately added.

The silylated monomers can be prepared by either of two general procedures:

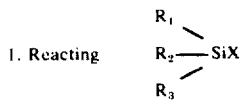

where X is halogen, usually chlorine or bromine, with a compound of the formulae:

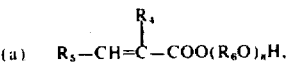

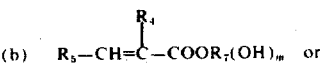

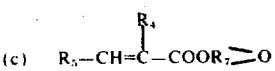

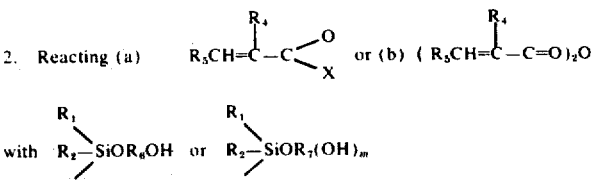

Examples of suitable starting materials of the formula

are trimethylsilylchloride, triethylsilychloride, tripropylsilyl chloride, triisopropylsilyl chloride, tributylsilyl chloride, trihexylsilyl chloride, triphenylsilyl chloride, tri-p-tolysilyl chloride, trimethylsilyl bromide, triethylsilyl bromide, dimethylethylsilyl chloride, dimethylpropylsilyl bromide, diethylpropylsilyl chloride, dimethylphenylsilyl chloride, dimethyl phenylsilyl bromide.

Examples of suitable starting materials of the formula

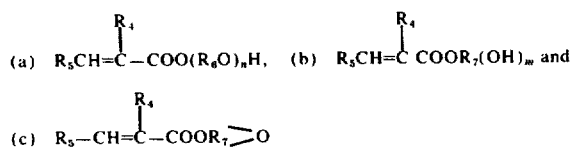

are hydroxyethyl acrylate, hydroxyethyl methacrylate, hydroxypropyl acrylate, hydroxypropyl methacrylate, hydroxybutyl acrylate, hydroxybutyl methacrylate, hydroxyethoxyethyl acrylate, hydroxyethoxyethyl methacrylate, hydroxyethoxyethoxyethyl acrylate, hydroxyethoxyethoxyethyl methacrylate, hydroxypropoxypropyl acrylate, hydroxypropoxypropyl methacrylate, hydroxyethoxyethoxyethyl methacrylate, hydroxy-2-chloropropylacrylate, hydroxy-2-chloro-propyl methacrylate, hydroxy-3-chlorobutyl acrylate, 2,3-dihydroxypropyl acrylate, 2,3-dihydroxypropyl methacrylate, 1,3-dihydroxypropyl methacrylate, trihydroxyneopentyl acrylate (pentaerythritol monoacrylate), pentaerythritol monomethacrylate, trimethylolpropane monoacrylate (dihydroxyneohexyl acrylate), sorbitol monomethacrylate, sorbitol monoacrylate, trimethylolpropane monomethacrylate, trimethyloethane monoacrylate, trimethylolethane monomethacrylate, hydroxyethyl chloroacrylate, hydroxypropyl chloroacrylate, hydroxyethoxyethyl chloroacrylate, hydroxypropoxypropyl chloroacrylate, hydroxyethyl fluoroacrylate, hydroxypropyl fluoroacrylate, hydroxyethoxyethyl fluoroacrylate, hydroxyethyl bromoacrylate, hydroxyethyl cyanoacrylate, hydroxypropyl cyanoacrylate, hydroxyethoxyethyl cyanoacrylate, hydroxyethyl phenylacrylate, hydroxypropyl phenylacrylate, hydroxyethoxyethyl phenylacrylate, hydroxyethyl crotonate, hydroxypropyl crotonate, hydroxyethoxyethyl crotonate, hydroxyethyl hexene-2-oate, 2,3-dihydroxypropyl fluoroacrylate, 2,3-dihydroxypropyl chloroacrylate, 2,3-dihydroxypropyl cyanoacrylate, 2,3-dihydroxypropyl phenylacrylate, 2,3-dihydroxypropyl crotonate, pentaerythritol monofluoroacrylate, pentaerythritol monochloroacrylate, pentaerythritol monocyanoacrylate, pentaerythritol monophenyl acrylate, pentaerythritol monocrotonate, trimethylolpropane monoacrylate, trimethylolethane monomethacrylate trimethylolethane monochloroacrylate, trimethylolpropane monofluoroacrylate, trimethylolethane monocyanoacrylate, trimethylolpropane monophenylacrylate, hydroxyethyl ethacrylate, hydroxypropyl ethacrylate, hydroxyethoxyethyl ethacrylate, 2,3-dihydroxypropyl ethacrylate, pentaerythritol monoethacrylate, hydroxyethyl propacrylate, glycidyl acrylate, glycidyl methacrylate, glycidyl fluoroacrylate, glycidyl chloroacrylate, glycidyl crotonate, glycidyl cyanoacrylate, glycidyl ethacrylate.

These compounds can be prepared in conventional fashion by esterifying the appropriate unsaturated acid, acid halide or acid anhydride with the appropriate polyhydric alcohol.

Examples of suitable starting materials of the formula

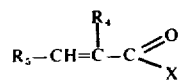

are methacrylyl chloride, methacrylyl bromide, acrylyl chloride, acrylyl bromide, crotonoyl chloride, cyanoacryloyl chloride, fluoroacrylyl bromide, chloroacrylyl chloride, ethacrylyl chloride, phenylacrylyl chloride.

Examples of suitable starting materials of the formula

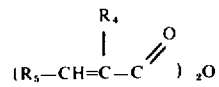

are methacrylic anhydride, acrylic anhydride, crotonic anhydride, fluoroacrylic anhydride, chloroacrylic anhydride, ethacrylic anhydride and phenylacrylic anhydride.

Examples of suitable starting materials of the formula

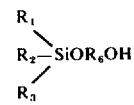

are trimethylsiloxyethanol, trimethylsiloxypropanol, trimethylsiloxyethoxyethanol, trimethylsiloxyethoxyethoxyethanol, trimethylsiloxyethoxyethoxyethoxyethanol, trimethylsiloxypropoxypropanol, trimethylsiloxypropan-2,3-diol, trimethylsiloxyneopentanediol, trimethylsiloxyneopentanetriol, dimethylethylsiloxyethanol, triethylsiloxypropanol, trimethylsiloxyneohexanediol, trimethylsiloxyhexanepentaol, dimethylphenylsiloxyethanol, dimethylphenylsiloxypropanol, dimethylphenylsiloxyethoxyethanol, tributylsiloxyethanol.

The pH is not critical for hydrolysis of silylated polymers. Thus, the pH can be from 1 to 14. Preferably the pH is from 1–5 or 8–14 in order to increase the speed of hydrolysis. However, hydrolysis can be accomplished even in pure water (pH 7) but the rate of hydrolysis is much slower, e.g., 24 hours against 1 hour for the same silylated polymer hydrolyzed at a pH of 4 at the same temperature. Hydrolysis can even be accomplished with humid air. Hydrolysis can be carried out at room temperature or elevated temperature, with an increase in temperature increasing the speed of hydrolysis. Thus, hydrolysis occurs very rapidly at the boiling point. Hydrolysis can be carried out for example, using water or aqueous alcohols, e.g., aqueous methanol, ethanol, isopropanol or propanol. Generally the amount of alcohol is 0 to 60% by weight of the water-alcohol since above 60% of the alcohol the rate of hydrolysis is very slow.

For hydrolysis of the polymer there can be used any convenient acid or base to provide the appropriate pH. Thus, there can be used acetic acid, propionic acid, chloroacetic acid, citric acid, lactic acid, sulfuric acid, phosphoric acid, hydrochloric acid, sodium hydroxide, ammonium hydroxide, potassium hydroxide, sodium carbonate, triethyl amine, ethylamine, butylamine, aniline, trimethylamine, diethylamine, benzenesulfonic acid, trichloroacetic acid, p-toluene sulfonic acid, etc.

Polymerization of the silylated monomers can be carried out in conventional manner using conventional free radical initiators, radiation or anionic initiators. Thus, there can be used per compounds such as benzoyl peroxide, diisopropyl percarbonate, diethyl percarbonate, potassium persulfate, ammonium persulfate, methyl ethyl ketone peroxide, cumene hydroperoxide, 2,4-dichlorobenzoyl peroxide, dicumyl peroxide, t-butyl peroctoate, t-butyl hydroperoxide, peracetic acid as well as redox system, e.g., a mixture of dibenzoyl peroxide or diisopropyl percarbonate with p-toluene sulfinic acid or potassium pyrosulfite; azo compounds (for example any of those mentioned in Hunt U.S. Pat. No. 2,471,909) e.g., azo-bisisobutyronitrile, methyl azo-bis-isobutyrate, ultra violet light, gamma rays, and other irradiation, e.g., high energy irradiation to an extent of 0.01 megarad or higher, e.g., 2 or 20 megarad, etc.

Polymerization in the presence of the hydrophobic polymer can be carried out to form linear homo or copolymers with 1,2,3,4 or more copolymerizable monomers which are solvent soluble or can be carried out in the presence of cross-linkers to form branched or three-dimensional insoluble products. The starting silylated monomer may also be copolymerized with one or more others with similar or different types in order to modify the properties. The choice of monomers makes possible the regulation of the hydrophilic properties of final polymeric products after hydrolysis. If comonomers are employed which give polymers having hydrophobic properties they should not be used to such an extent that the hydrophilic properties of the hydrolyzed silylated copolymer are lost.

The copolymers normally contain 0.1 to 50% of the copolymerizable monomer or monomers, usually 0.2 to 20% on a molar basis. When a cross-linking monomer is present it usually is employed in an amount of 0.1 to 2% but it can be employed in an amount of 5% or more. Both linear and cross-linking monomers can be present at the same time, e.g., a terpolymer can be made from 90% trimethylsiloxyethyl methacrylate, 9.5% methyl methacrylate and 0.5% ethylene glycol dimethacrylate by weight. As copolymerizable materials there can be used, for example, acrylonitrile, methacrylonitrile, (preferably up to 40 mol %), styrene, p-methyl styrene, alpha methyl styrene, methyl methacrylate, butyl methacrylate, methyl acrylate, ethyl acrylate, butyl acrylate, allyl acetate, 2-ethylhexyl acrylate, methacrylic acid (up to 50 mol % for best results), acrylic acid, vinyl acetate, vinyl chloride, itaconic acid, maleic anhydride, fumaric acid, vinylidene chloride, vinyl pyridine, methoxyethyl acrylate, methoxyethyl methacrylate, ethoxyethyl acrylate, ethoxyethyl methacrylate, ethoxyethoxyethyl methacrylate, vinyl pyrrolidone, monohydroxyethyl maleate.

As cross-linking monomers there can be used, for example, compounds containing a plurality of ethylenically unsaturated double bonds such as ethylene glycol diacrylate, ethylene glycol dimethacrylate, butylene diacrylate, 1,2-butylene dimethacrylate, diethylene glycol diacrylate, diethylene glycol dimethacrylate, triallyl melamine, N,N'-methylene bis acrylamide, N,N'-methylene bis methacrylamide, glycerine trimethacrylate, pentaerythritol tetraacrylate, trimethylolethane trimethacrylate, triethylene glycol dimethacrylate, trimethylolpropane triacrylate, diallyl maleate, diallyl monoglycol citrate, allyl vinyl malate, diallyl ether, divinyl ether, divinyl sulfone, hexahydro-1,3,3-triacrylyltriazine, propylene glycol diacrylate, diallyl tartrate, diallyl itaconate, diallyl sucrose, sucrose diacrylate, glucose dimethacrylate, triallyl glucose, diallyl benzenephosphonate.

Unless otherwise indicated all parts and percentages are by weight.

The products of the invention can be employed for the same uses as the corresponding hydrophilic linear or cross-linked polymers of Wichterle U.S. Pat. No. 2,976,576, Wichterle Reissue U.S. Pat. No. Re. 27,401; Gould U.S. Pat. No. 3,400,890; Shepherd U.S. Pat. No. 3,428,043; Shepherd U.S. Pat. No. 3,470,883; Wichterle U.S. Pat. No. 3,476,499; Shepherd U.S. Pat. No. 3,488,215; Shepherd U.S. Pat. No. 3,515,579; Shepherd U.S. Pat. No. 3,520,949; Kliment U.S. Pat. No. 3,551,556; Kliment U.S. Pat. No. 3,563,925; Shepherd U.S. Pat. No. 3,566,874; Shepherd U.S. Pat. No. 3,567,118; Shepherd U.S. Pat. No. 3,574,822; Shepherd U.S. Pat. No. 3,574,826; Shepherd U.S. Pat. No. 3,575,123; Gould U.S. Pat. No. 3,576,760; Shepherd U.S. Pat. No. 3,577,512; Shepherd U.S. Pat. No. 3,577,516; Shepherd U.S. Pat. No. 3,577,518; Gould U.S. Pat. No. 3,596,833; Kugler U.S. Pat. No. 3,597,384; Guttag U.S. Pat. No. 3,615,595; Shepherd U.S. Pat. No. 3,618,213; Stol U.S. Pat. No. 3,620,751; Stoy U.S. Pat. No. 3,625,741; Stol U.S. Pat. No. 3,628,988; Chromacek U.S. Pat. No. 3,632,381; Shepherd U.S. Pat. No. 3,632,416; Guttag U.S. Pat. No. 3,633,546; Gould U.S. Pat. No. 3,641,237; Shepherd U.S. Pat. No. 3,660,218; DeLong U.S. Pat. No. 3,669,691; Shepherd U.S. Pat. No. 3,674,901; Wichterle U.S. Pat. No. 3,679,504; Kliment U.S. Pat No. 3,689,634; Shepherd U.S. Pat. No. 3,697,643 and Wichterle U.S. Pat. No. 3,699,089.

Unless otherwise indicated all parts and percentages in the specification and claims are by weight.

EXAMPLE 1

The silylated monomers set forth at the end of the example were prepared by the following procedure:

1 mole of the hydroxyester, i.e. hydroxyethyl acrylate, hydroxyethyl, hydroxypropyl acrylate, hydroxypropyl methacrylate, methacrylate, hydroxyethoxyethyl acrylate, hydroxyethoxyethyl methacrylate, or hydroxyethoxyethoxyethyl methacrylate was mixed with 2.3 moles of triethylamine and 200 ml of hexane. The mixture was cooled to approximately 10°C. and 1 mole of the trihydrocarbyl silane chloride, i.e. trimethylsilane chloride, dimethylethylsilane chloride or dimethylphenylsilane chloride was added dropwise with stirring. The precipitated amine hydrochloride was filtered off. (While triethylamine was used in the working examples, there can be used any other tertiary amine, e.g. trimethylamine, tributylamine, N,N-dimethylamiline, as well as primary amines, e.g. ethylamine or diethylamine, or other alkaline material forming a hydrocarbon insoluble chloride salt). The precipitated amine hydrochloride was filtered off, washed with hexane and the combined filtrates were washed with ice cold water as fast as possible several times. The hexane layer was dried with anhydrous $MgSO_4$, filtered and the hexane evaporated to yield a clear liquid which was vacuum distilled and refractionated. Due to the very different boiling point of the silylated monomer and that of any cross-linking monomer present, the product obtained in each case exhibited a negligible cross-linker peak.

The compounds recovered were as set forth below in the table.

Table

| (a) | Trimethylsiloxyethyl acrylate | b.p. 38/0.3 mm |
|---|---|---|
| (b) | Trimethylsiloxyethyl methacrylate | b.p. 40/0.3 mm |
| (c) | Trimethylsiloxypropyl acrylate | b.p. 43/0.1 mm |
| (d) | Trimethylsiloxypropyl methacrylate | b.p. 44/0.1 mm |

Table-continued

| | | |
|---|---|---|
| (e) | Dimethylethylsiloxyethyl acrylate | b.p. 40/0.3 mm |
| (f) | Dimethylphenylsiloxy ethyl acrylate | b.p. 78/0.1 mm |
| (g) | Trimethylsiloxyethoxyethyl methacrylate | b.p. 72/0.3 mm |
| (h) | Trimethylsiloxyethoxyethyl acrylate | b.p. 68/0.3 mm |
| (i) | Trimethylsiloxyethoxyethoxyethyl methacrylate | b.p. 85/0.3 mm |

In examples 1 (a), (b), (c), (d), (g), (h) and (i) there was employed trimethylsilane chloride, in example 1(e) there was used dimethylethylsilane chloride and in example 1(f) there was used dimethylphenylsilane chloride. In examples 1(a), (e) and (f) there was used hydroxyethyl acrylate, in example 1(b) hydroxyethyl methacrylate, in example 1(c) hydroxypropyl acrylate, example 1(d) hydroxypropyl methacrylate, in example 1(g) hydroxyethoxyethyl methacrylate, example 1(h) hydroxyethoxyethyl acrylate and example 1(i) hydroxyethoxyethoxyethyl methacrylate.

EXAMPLE 2

The same silylated monomers were prepared as in example 1, but by reacting 1 mole of the acrylyl chloride or methacrylyl chloride with 1 mole of the appropriate trihydrocarbylsiloxyalkanol in benzene in the presence of triethylamine.

In a specific illustration 1 mole of methacrylyl chloride diluted with the same volume of benzene was added dropwise to a stirred and cooled (about 10°C.) mixture of 1 mole of trimethylsiloxyethanol and 2 moles of dry triethylamine diluted with the same volume of dry benzene. Stirring was continued at room temperature for 2 hours. The separated amine hydrochloride was filtered off, and the precipitate washed with benzene and the combined filtrates were washed with ice cold water as fast as possible several time. The benzene layer was dried with anhydrous $MgSO_4$, filtered, the benzene evaporated to yield a clear liquid, which was vacuum distilled and refractionated to give trimethylsiloxyethyl methacrylate.

EXAMPLE 3

A natural latex article was extracted by chloroform to remove all nonpolymeric components, dried to constant weight and immersed into a solution of 100 parts of trimethylsiloxyethyl acrylate, containing 0.5 parts of triglycol diacrylate and 0.5 parts of methyl azo-bis-isobutyrate (initiation) for 24 hours. Excess monomer was removed from the surface and the article was heated in an inert atmosphere at 80°C for 4 hours in the presence of additional monomer with initiator in the vessel to eliminate loss of monomer from the article by evaporation. The surface layer was hydrolyzed in 5% acetic acid for 24 hours and washed in water for 72 hours to give the hydroxyethyl acrylate polymer coated rubber article. Illustrative articles which can be used include diaphragms, rubber tubing (including catheters) which can be coated either externally, internally or both.

EXAMPLE 4

A silicon rubber (polydimethyl siloxane) article was extracted by ethanol to remove all nonpolymeric components, dried to constant weight and immersed into a solution of 100 parts of trimethylsiloxypropyl acrylate containing 0.5 parts of ethylene glycol dimethacrylate and 0.5 parts of methyl azo-bis-isobutyrate for 4 hours.

The article was then treated as in Example 3. Thus a silicone rubber gasket could be the article treated.

EXAMPLE 5

A polypropylene article was extracted by isopropanol to remove nonpolymeric components, dried and immersed into a solution of 100 parts of trimethylsiloxyethyl methacrylate containing 0.5 parts of divinyl benzene and 0.5 parts t-butyl peroctoate for 8 hours. The article was then treated as in Example 3. The initiator was removed by alcohol extraction. The product was hydroxyethyl methacrylate polymer coated polypropylene. Illustrative articles are polypropylene fibers, films and tubing.

EXAMPLE 6

A sheet of clear polystyrene was immersed into a solution of 100 parts of trimethylsiloxyethoxyethyl acrylate containing 0.5 parts of ethylene glycol dimethacrylate and 0.5 parts of methyl azo-bis-isobutyrate for 12 hours. It was subsequently exposed at room temperature to long wave UV light in a vessel with inert atmosphere and covered with a transparent lid. After the polymerization was finished, the sheet was treated as in Example 3. There was obtained a sheet of polypropylene having bonded thereto a film of hydroxyethoxyethyl acrylate ethylene dimethacrylate copolymer.

EXAMPLE 7

A sheet of ethylene-propylene copolymer was extracted by isopropanol to remove all nonpolymeric components and immersed into a solution of 100 parts of trimethylsiloxypropyl methacrylate containing 0.5 parts of glycol dimethacrylate and 0.5 parts of methyl azo-bis-isobutyrate for 4 hours. It was then irradiated by gamma rays in an inert atmosphere for the period of time necessary to effect polymerization. In this case polymerization was generally much faster than degradation or cross-linking of the substrate. The sheet was then treated as in Example 3.

Coatings of hydrophilic copolymers of any of the hydrolyzed silylated acrylates or methacrylates with any of the other monomers mentioned above can be prepared in the same manner as Examples 4–7 by replacing the comonomer, e.g., ethylene glycol dimethacrylate by a different comonomer, e.g., ethyl acrylate, methoxyethyl methacrylate, styrene, vinyl chloride, vinylpyrrolidone, etc.

The hydrophobic polymers which are treated according to the invention are solid polymers. Likewise the hydrophilic polymers obtained are solids.

As used in the claims the term "coating" is generic to graft type coatings and non-graft coatings.

What is claimed is:

1. A process for preparing a hydrophobic polymer substrate having a coating thereon of a hydrophilic polymer selected from the group consisting of homopolymers and copolymers comprising (A) coating said substrate with material selected from the group consisting of (1) a silylated monomer having the formula:

(a) 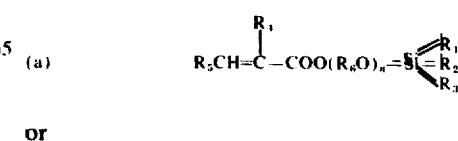

or (b) 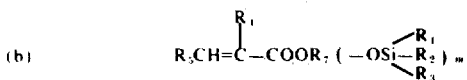

and (2) a mixture of said silylated monomer and a copolymerizable monomer; wherein $R_5$ is hydrogen or lower alkyl; $R_4$ is hydrogen, lower alkyl, halogen of atomic weight 9 to 80, phenyl or cyano, $R_6$ is alkylene or haloalkylene of 2 to 4 carbon atoms; $R_7$ is alkylene of 3 to 6 carbon atoms; $n$ is an integer of 1 to 4; $m$ is an integer of 2 to 5; and $R_1$, $R_2$ and $R_3$ are lower alkyl, pehnyl, or tolyl; (B) hydrolyzing the polymerized monomer or mixtures of monomers to form the hydrophilic polymer by replacing the

groups by hydrogen atoms.

2. The product prepared by the process of claim 1.

3. The process of claim 1, where $R_5$ is hydrogen and $R_4$ is hydrogen or methyl.

4. The product prepared by the process of claim 3.

5. The process of claim 1, wherein the hydrophilic polymer formed is a homopolymer.

6. The product prepared by the process of claim 5.

7. The process of claim 1, wherein the hydrophilic polymer is a copolymer prepared by copolymerizing the silylated monomer with 0.1 to 50% on a molar basis of a copolymerizable monomer.

8. The product prepared by the process of claim 7.

9. The process of claim 7, wherein the copolymerizable monomer is present in an amount of 0.1 to 20% on a molar basis and is an ethylenically unsaturated cross-linking material.

10. The process of claim 1, wherein the silylated monomer has formula (1).

11. The process of claim 10 wherein $R_5$ is hydrogen, $R_4$ is hydrogen or methyl, $n$ is 2 to 3 and $R_6$ is alkylene.

12. The process of claim 11, wherein two of the $R_1$, $R_2$, and $R_3$ members are from the group consisting of methyl and ethyl.

13. The process of claim 1, wherein the hydrophobic polymer substrate is a hydrocarbon polymer.

14. The product prepared by the process of claim 13.

15. The process of claim 13, wherein the hydrocarbon polymer is natural rubber, polyisobutylene, polystyrene, polyethylene, polypropylene, ethylene-propylene copolymer, ethylene-propylene-non-conjugated polyene terpolymer, butyl rubber, butadiene-styrene copolymer or cis-isoprene polymer.

16. The process of claim 1, wherein the hydrophobic polymer substrate is a silicone rubber.

17. The product prepared by the process of claim 16.

18. The process of claim 1, wherein the hydrophobic polymer substrate is a butadiene-acrylonitrile copolymer, a perfluorinated hydrocarbon polymer, a polyester, an acrylonitrile polymer, nylon, a vinyl chloride polymer, a polymer of an alkyl acrylate or methacrylate.

19. The product prepared by the process of claim 18.

20. The process of claim 1, wherein the pH is other than 5.5 to 8.5.

21. A process according to claim 1 wherein the composition employed for said coating consists essentially of said monomer or monomers.

22. A process according to claim 21 wherein the composition employed for said coating consists of (1) said monomer or monomers and (2) a free radical initiator.

* * * * *